(12) United States Patent
Heinrich et al.

(10) Patent No.: US 9,186,043 B2
(45) Date of Patent: Nov. 17, 2015

(54) LAPAROSCOPIC SCAFFOLD ASSEMBLY

(71) Applicant: Covidien LP, Mansfield, MA (US)

(72) Inventors: Russell S. Heinrich, Madison, CT (US); Frank Viola, Sandy Hook, CT (US); Eric Alexander Stanley, Milford, CT (US)

(73) Assignee: Covidien LP, Mansfield, MA (US)

( * ) Notice: Subject to any disclaimer, the term of this patent is extended or adjusted under 35 U.S.C. 154(b) by 295 days.

(21) Appl. No.: 14/030,270

(22) Filed: Sep. 18, 2013

(65) Prior Publication Data

US 2014/0018614 A1 Jan. 16, 2014

Related U.S. Application Data

(62) Division of application No. 12/942,046, filed on Nov. 9, 2010, now Pat. No. 8,551,078.

(60) Provisional application No. 61/266,994, filed on Dec. 4, 2009.

(51) Int. Cl.

| A61B 1/00 | (2006.01) |
|---|---|
| A61B 17/00 | (2006.01) |
| A61B 17/02 | (2006.01) |
| A61B 19/02 | (2006.01) |
| A61B 19/00 | (2006.01) |

(52) U.S. Cl.
CPC ........... *A61B 1/00105* (2013.01); *A61B 1/0011* (2013.01); *A61B 17/00234* (2013.01); *A61B 17/0218* (2013.01); *A61B 19/026* (2013.01); *A61B 19/22* (2013.01); *A61B 19/5212* (2013.01); *A61B 2017/00221* (2013.01); *A61B 2017/00283* (2013.01); *A61B 2017/00398* (2013.01); *A61B 2019/2215* (2013.01); *A61B 2019/2226* (2013.01); *A61B 2019/2242* (2013.01); *A61B 2019/5206* (2013.01); *Y10T 29/49826* (2015.01)

(58) Field of Classification Search
CPC ........................ A61B 1/00105; A61B 1/0011
See application file for complete search history.

(56) References Cited

U.S. PATENT DOCUMENTS

| 4,625,938 A | 12/1986 | Brown | |
|---|---|---|---|
| 4,710,819 A | 12/1987 | Brown | |
| 4,829,999 A * | 5/1989 | Auth | A61M 25/013 24/115 R |
| 5,053,041 A * | 10/1991 | Ansari | A61B 17/29 606/1 |

(Continued)

FOREIGN PATENT DOCUMENTS

| WO | 93/18712 A1 | 9/1993 |
|---|---|---|
| WO | 2009/019288 A2 | 2/2009 |

OTHER PUBLICATIONS

The extended International Search Report corresponding to European Application No. 10 25 2055.8, completed Apr. 13, 2011; mailed Apr. 19, 2011; (4 Pages).

*Primary Examiner* — Christian Sevilla

(57) ABSTRACT

A scaffold assembly includes an instrument pod and a plurality of actuable movers. The instrument pod may include one or more instruments operably coupled thereto. The instrument pod is inserted through a tissue tract into the body cavity. Each actuatable mover includes an insertion member extending therefrom for insertion within tissue. Each mover has one or more lines removably attachable to the instrument pod that are configured to move the instrument pod between different positions relative to each mover upon the actuation of one or more of the movers to move the instrument pod within the body cavity.

19 Claims, 9 Drawing Sheets

(56) References Cited

U.S. PATENT DOCUMENTS

| | | | | |
|---|---|---|---|---|
| 5,224,426 | A | | 7/1993 | Rodnunsky et al. |
| 5,275,605 | A | * | 1/1994 | Winkler .................. A61B 17/22 604/908 |
| 5,304,183 | A | * | 4/1994 | Gourlay ........... A61B 17/00234 227/901 |
| 5,582,607 | A | * | 12/1996 | Lackman .............. A61F 2/2427 606/1 |
| 5,709,675 | A | * | 1/1998 | Williams ............... A61B 18/00 604/22 |
| 5,921,979 | A | * | 7/1999 | Kovac .................... A61B 17/02 606/1 |
| 5,984,866 | A | * | 11/1999 | Rullo ...................... A61B 17/02 600/227 |
| 6,149,642 | A | * | 11/2000 | Gerhart ........... A61B 17/00234 128/897 |
| 6,939,296 | B2 | * | 9/2005 | Ewers ...................... A61B 1/06 128/849 |
| 6,945,932 | B1 | * | 9/2005 | Caldwell ............ A61B 17/3423 600/208 |
| 7,976,565 | B1 | * | 7/2011 | Meridew ............ A61B 17/0401 606/1 |
| 8,551,078 | B2 | * | 10/2013 | Heinrich .......... A61B 17/00234 600/201 |
| 2003/0208187 | A1 | * | 11/2003 | Layer .................... A61B 19/201 606/1 |
| 2004/0176751 | A1 | * | 9/2004 | Weitzner ............ A61B 17/0469 606/1 |
| 2005/0154413 | A1 | * | 7/2005 | Trabada .............. A61B 1/00147 606/190 |
| 2006/0030841 | A1 | * | 2/2006 | Madhani .......... A61B 17/00234 606/1 |
| 2007/0172803 | A1 | * | 7/2007 | Hannaford ........... G09B 23/285 434/262 |
| 2009/0048612 | A1 | * | 2/2009 | Farritor .............. A61B 19/2203 606/130 |
| 2010/0174244 | A1 | * | 7/2010 | Dankelman ............ A61B 19/38 604/264 |
| 2010/0222772 | A1 | * | 9/2010 | Kleshinski ........ A61B 17/12022 606/1 |
| 2011/0137129 | A1 | * | 6/2011 | Heinrich ............ A61B 1/00105 600/206 |
| 2011/0264078 | A1 | * | 10/2011 | Lipow .................. A61B 19/201 606/1 |
| 2012/0095449 | A1 | * | 4/2012 | Stefanchik ......... A61B 17/0218 606/1 |
| 2012/0116362 | A1 | * | 5/2012 | Kieturakis ............. A61B 17/29 606/1 |
| 2013/0023860 | A1 | * | 1/2013 | Nagashimada ........ A61B 19/22 606/1 |

\* cited by examiner

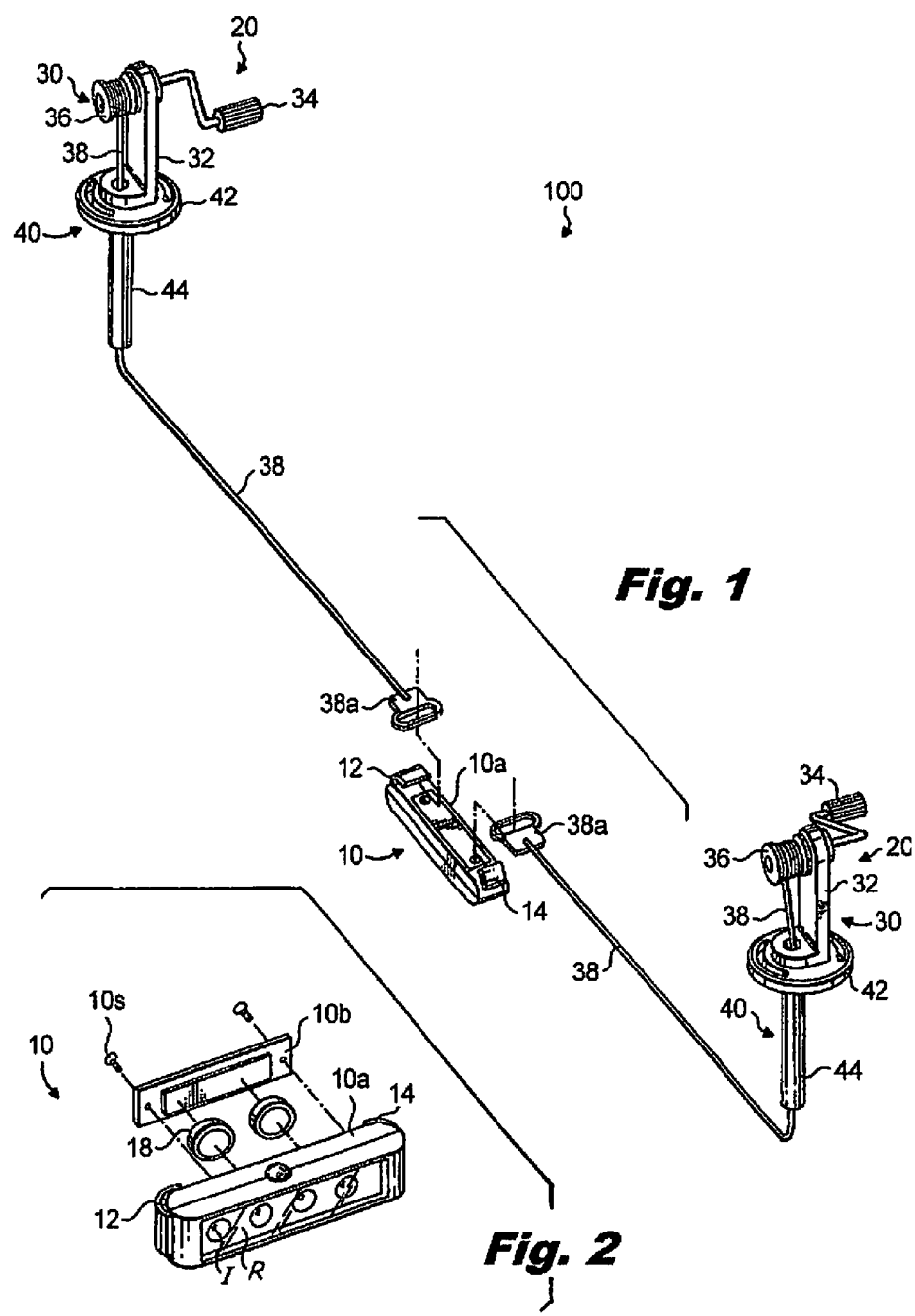

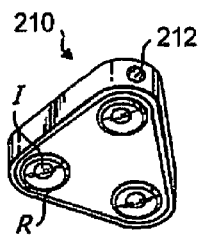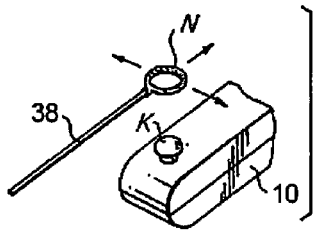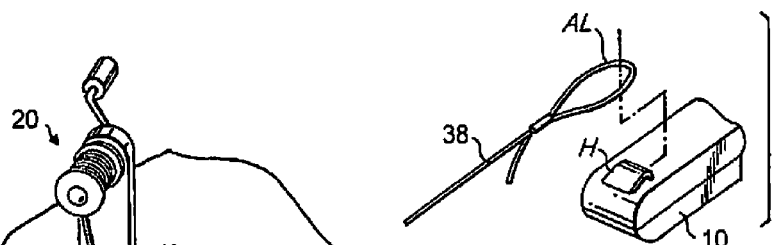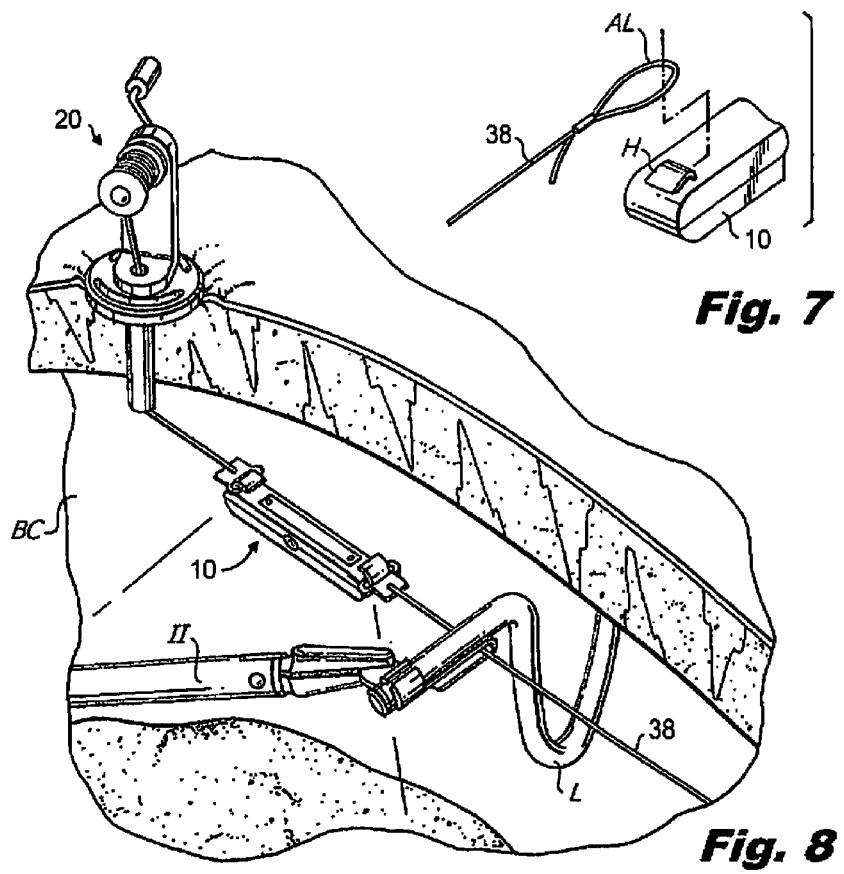

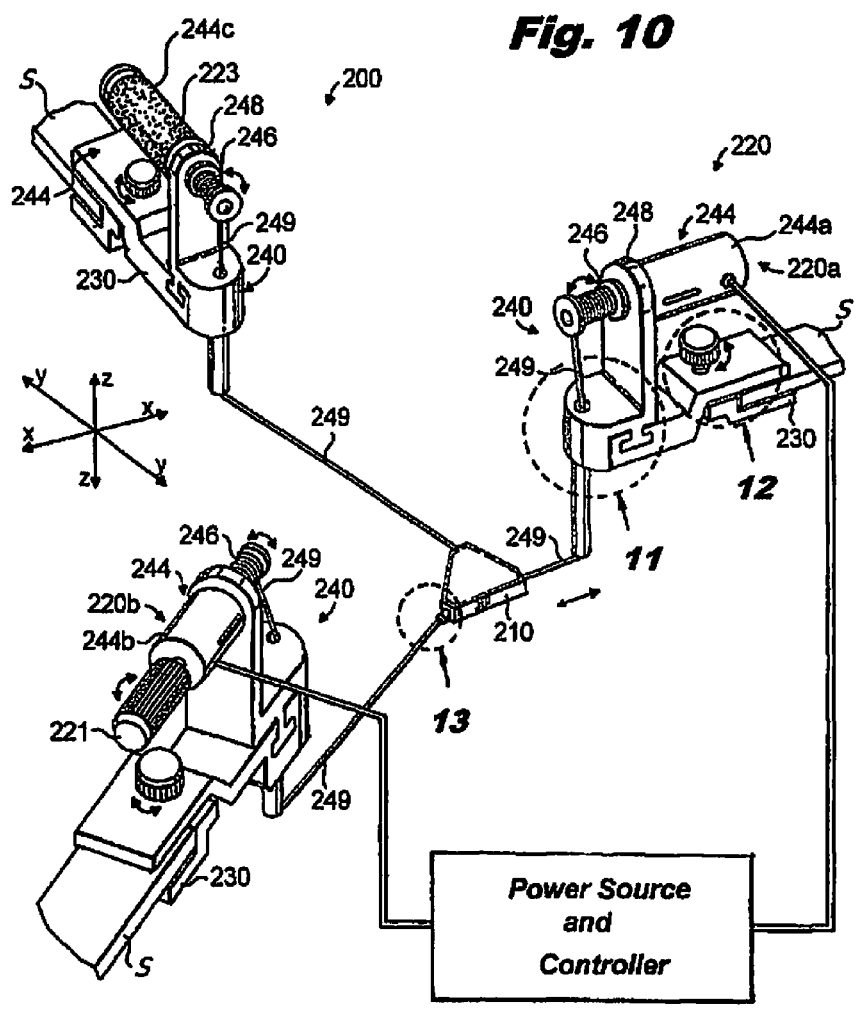

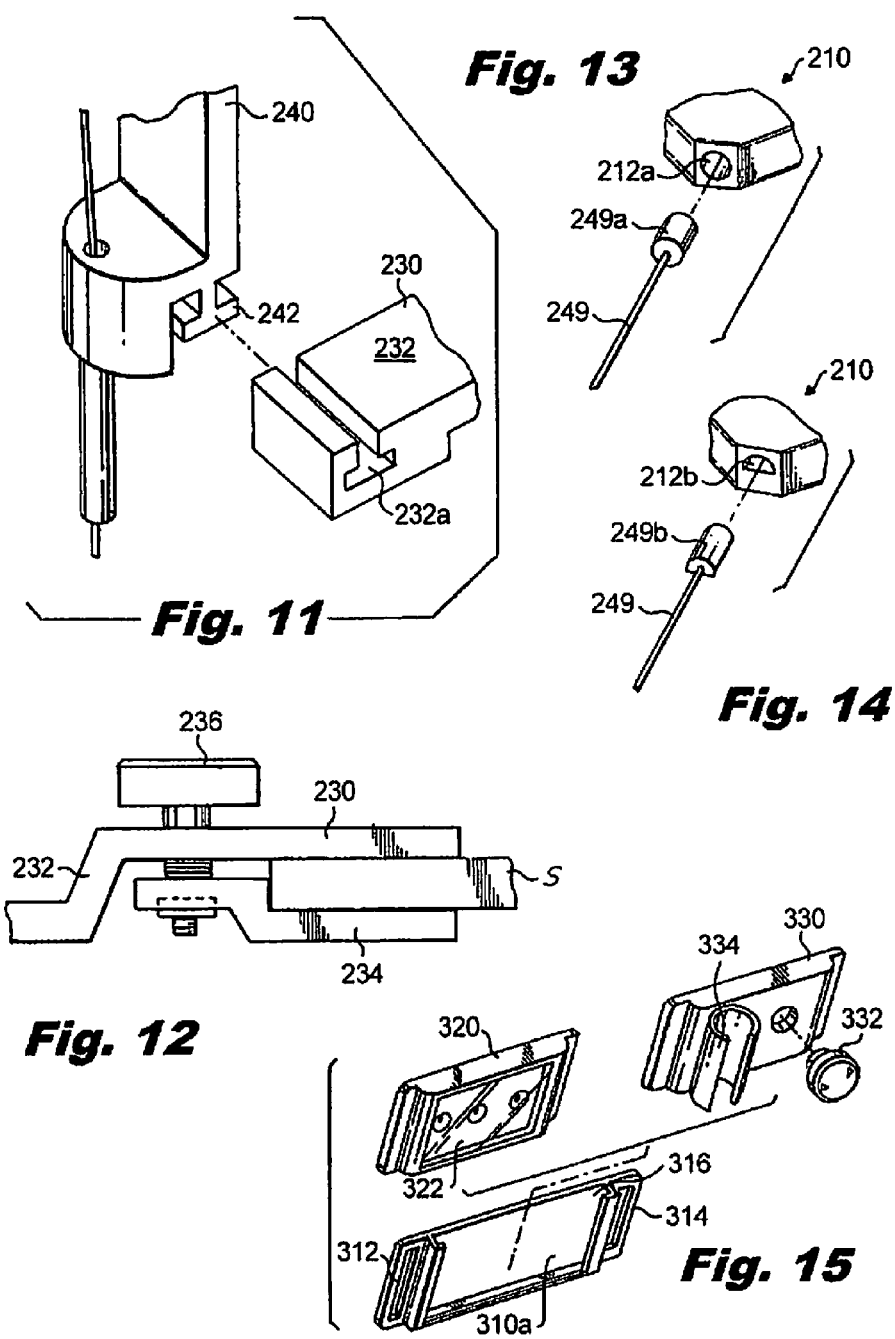

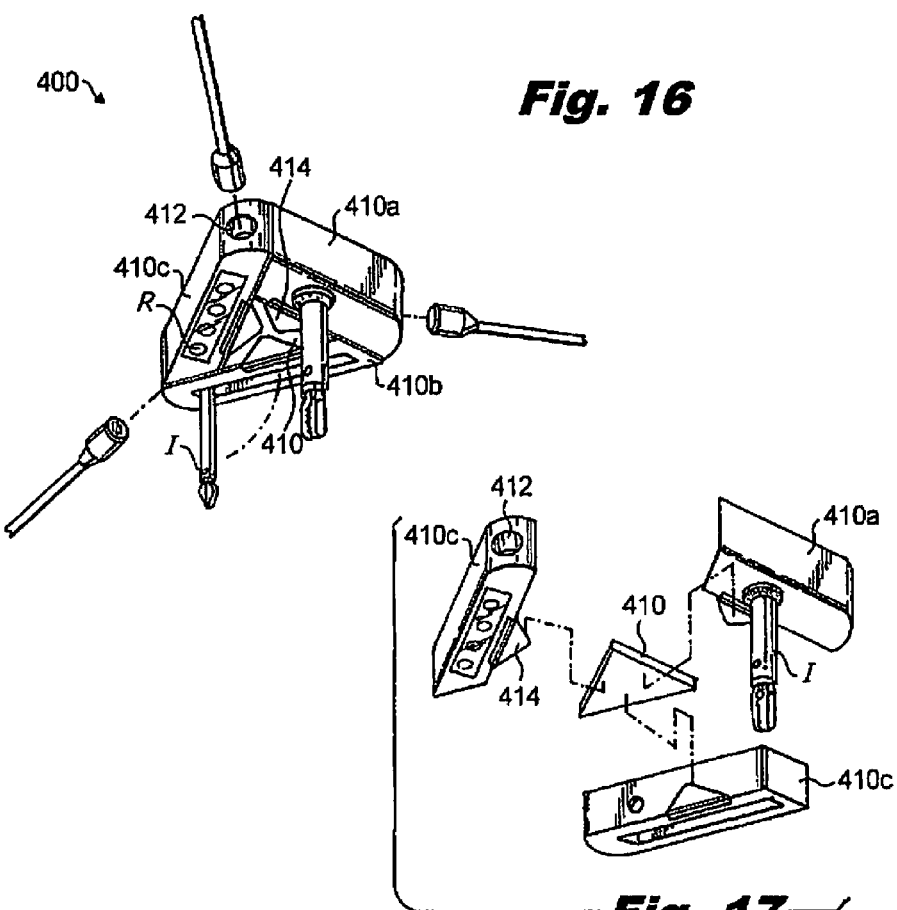
Fig. 16
Fig. 17
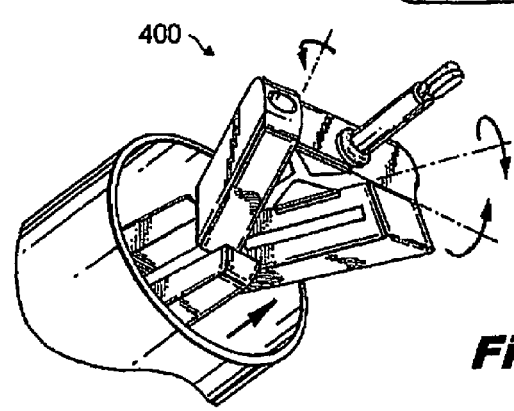
Fig. 18

LAPAROSCOPIC SCAFFOLD ASSEMBLY

CROSS REFERENCE TO RELATED APPLICATIONS

This application is a divisional of U.S. patent application Ser. No. 12/942,046, filed on Nov. 9, 2010, which claims the benefit of U.S. Provisional Application Ser. No. 61/266,994, filed on Dec. 4, 2009, the entire contents of which are incorporated herein by this reference.

BACKGROUND

1. Technical Field

This application generally relates to the field of minimally invasive surgery. More particularly, the present disclosure relates to an assembly and a method for providing power, data, illumination, and instrumentation into a body cavity.

2. Description of Related Art

Laparoscopy is a minimally invasive surgical procedure performed in the abdominal cavity. It has become the treatment of choice for several routinely performed interventions.

However, known laparoscopy technologies are limited in scope and complexity due in part to 1) mobility restrictions resulting from using rigid tools inserted through access ports, and 2) limited visual feedback. That is, long rigid laparoscopic tools inserted through small incisions in the abdomen wall limit the surgeon's range of motion and therefore the complexity of the surgical procedures being performed. Similarly, using a 2-D image from a typically rigid laparoscope inserted through a small incision limits the overall understanding of the surgical environment. Current technology requires a third port to accommodate a laparoscope (camera). Each new viewpoint requires an additional incision and thus, more pain and scarring for the patient and an added effort for the surgeon.

SUMMARY

Accordingly, a scaffold assembly for minimally invasive surgery, e.g. laparoscopic surgery, is provided and includes an instrument pod and a plurality of actuable movers. The instrument pod may include one or more instruments operably coupled thereto. The instrument pod is configured for insertion through a tissue tract into a body cavity. In some embodiments, the instrument pod is configured to fit through a cannula of an access device. The instrument pod may be configured to collapse for insertion and then expand inside the body cavity. In some embodiments, the instrument pod is selectively movable between two movers. In other embodiments, the instrument pod is selectively movable between three movers.

The instrument pod (support) can have an elongated configuration having first and second opposing end portions and a line of a first of the movers is attached at the first end portion and a line of a second of the movers is attached at a second end portion. The plurality of movers in one embodiment can comprise three movers and the instrument pod can have a substantially triangular configuration, a line of each of the movers attached adjacent a vertex of the instrument pod.

The plurality of actuable movers preferably each includes a cannula extending therefrom for insertion within tissue. Each mover preferably has at least one line removably attachable to the instrument pod and configured to move the instrument pod between different positions within the body cavity relative to each mover upon the actuation of at least one of the movers.

Each mover can be actuable manually, electrically or by other methods. Each manually actuable mover can include a handle or a knob. In some embodiments, a power source is operably connected to one or more of the electrically actuable movers. The one or more instruments supported by the instrument pod may include one or more of a camera, an illumination source, a grasper, a retractor, and a sensor. One or more movers may include a rotatable spool operably associated with the one or more lines. The one or more lines may include one or both of a fiber optic wire/cable or an electrical wire/cable which operably couple to one or more ports of the instrument pod. The one or more lines may be operably connected to a CPU controller. The one or more lines are preferably movable through the cannula of one of the respective movers. The one or more instruments are preferably selectively operable within the body cavity.

In another aspect, a method of movably suspending an instrument pod within a body cavity is disclosed which includes providing a scaffold assembly including an instrument pod and a plurality of movers. The instrument pod includes one or more instruments operably associated therewith. Each mover includes a cannula and at least one line extending therefrom. The at least one line is selectively extendable and retractable from each respective mover. The method includes inserting the instrument pod into a body cavity and attaching the at least one line of one or more of the movers to the instrument pod while the instrument pod and the at least one line is positioned within the body cavity. The method further includes selectively extending or retracting the one or more lines such that the instrument pod moves within the body cavity.

In some embodiments, the method includes selectively moving the instrument pod within the body cavity between two movers. In other embodiments, the method includes selectively moving the instrument pod within the body cavity between three movers. The method further includes selectively operating the one or more instruments within the body cavity wherein the one or more instruments may include one or more of a camera, an illumination source, a grasper, a retractor, and a sensor or the like.

BRIEF DESCRIPTION OF THE DRAWINGS

The above and other aspects, features, and advantages of the present disclosure will become more apparent in light of the following detailed description when taken in conjunction with the accompanying drawings in which:

FIG. 1 is a perspective view of one embodiment of a laparoscopic scaffold assembly having a pair of movers and an instrument pod in accordance with the present disclosure;

FIG. 2 is an enlarged perspective view, with parts separated, of the instrument pod of FIG. 1;

FIG. 6 is a partial perspective view of one embodiment of an instrument pod and a complimentary embodiment of a line of a mover in accordance with the present disclosure;

FIG. 7 is a partial perspective view of another embodiment of an instrument pod and a complimentary embodiment of a line of a mover in accordance with the present disclosure;

FIG. 8 is perspective view illustrating an accessory light being hung on a line within a body cavity in accordance with the principles of the present disclosure;

FIG. 9 is a perspective view of another embodiment of an instrument pod in accordance with the present disclosure;

FIG. 10 is a perspective view of another embodiment of a laparoscopic scaffold assembly including manual and electrical movers each having an anchor portion and a moving portion in accordance with the present disclosure;

FIG. 11 is an enlarged, perspective view, with parts separated, of the area of detail of FIG. 10 showing the anchor portion and the moving portion of one of the movers;

FIG. 12 is an enlarged, partial side elevational view of the anchor portion of FIG. 10;

FIG. 13 is an enlarged, partial perspective view of one embodiment of an instrument pod and a complimentary mover line;

FIG. 14 is an enlarged, partial perspective view of another embodiment of an instrument pod and a complimentary mover line;

FIG. 15 is a perspective view of one embodiment of an instrument pod in accordance with the present disclosure;

FIG. 16 is a perspective view of another embodiment of an instrument pod positioned in a first condition in accordance with the present disclosure;

FIG. 17 is a perspective view, with parts separated, of the instrument pod of FIG. 16;

FIG. 18 is a perspective view of the instrument pod of FIGS. 16 and 17 positioned in a second condition for insertion through a cannula;

DETAILED DESCRIPTION

Figure 3:
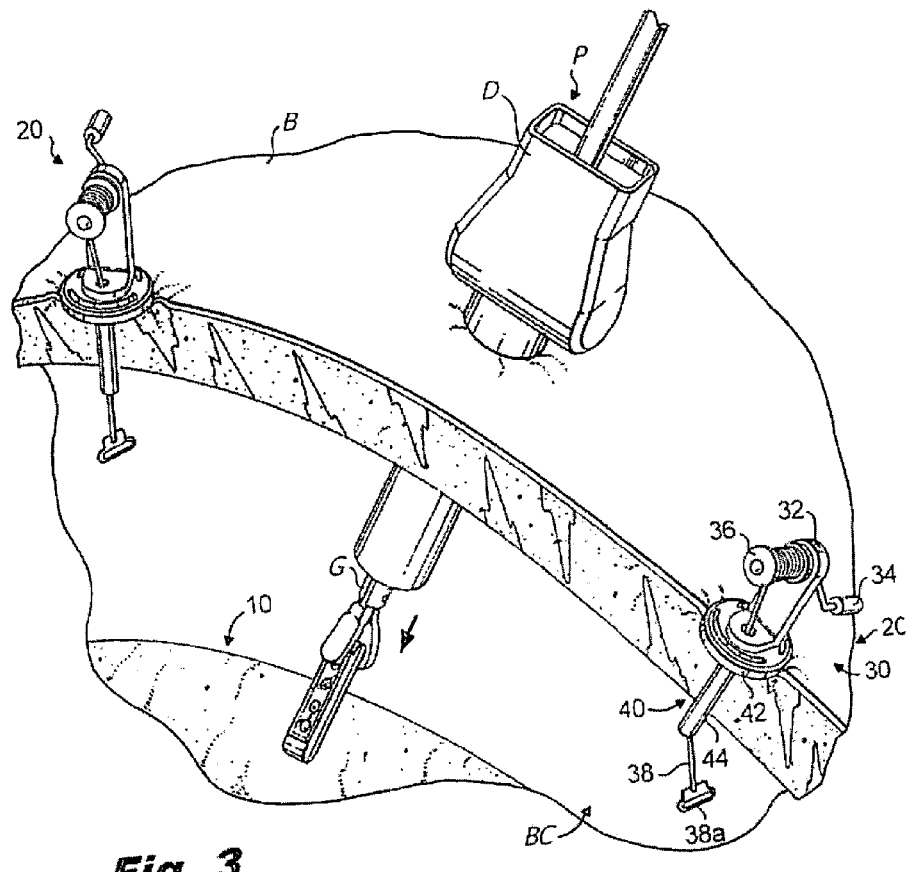
FIG. 3 is a perspective view of the laparoscopic scaffold assembly of FIG. 1 with the movers shown mounted to a patient's body and the instrument pod shown inserted by a grasper through an access device into a body cavity.

Various embodiments of the present disclosure will now be described in detail with reference to the drawings, wherein like reference numerals identify similar or identical elements. In the drawings and in the description that follows, the term "proximal," will refer to the end that is closer to the operator, while the term "distal" will refer to the end that is farther from the operator.

Turning now to FIG. 1, one embodiment of a laparoscopic scaffold assembly 100 includes an instrument pod 10 and two actuable movers 20. The instrument pod 10 includes a body portion 10a having a pair of catches 12, 14 extending from the distal ends thereof. The instrument pod 10 can have catches of any suitable shape such as a knob "K" illustrated in FIG. 6 or a curvilinear hook "H" illustrated in FIG. 7. As best shown in FIG. 2, the instrument pod 10 includes one or more receptacles "R" that are configured to receive one or more instruments "I" (see FIG. 16) therein. Examples of such instruments "I" include, but are not limited to, clip appliers, graspers, dissectors, retractors, staplers, laser probes, illumination sources, photographic devices, endoscopes and laparoscopes, tubes, and the like. The instrument pod 10 of FIG. 2 includes a plurality of instruments "I" affixed to the one or more receptacles "R", which are illumination sources (e.g., light bulbs). However, other instruments "I" may be mounted therein such as those discussed above and shown in FIG. 16. Some of these instruments (e.g. illumination sources such as light bulbs) may be powered by one or more batteries 18 housed within the instrument pod 10 by a back plate 10b that is held in position by one or more screws 10s. In addition, some of these instruments (e.g., photographic devices) operate on input/output type signal transmission. Accordingly, the instrument pod 10 may be configured to receive and send analog or digital signals through wired or wireless transmissions which will be described in greater detail hereinbelow.

Figure 20:
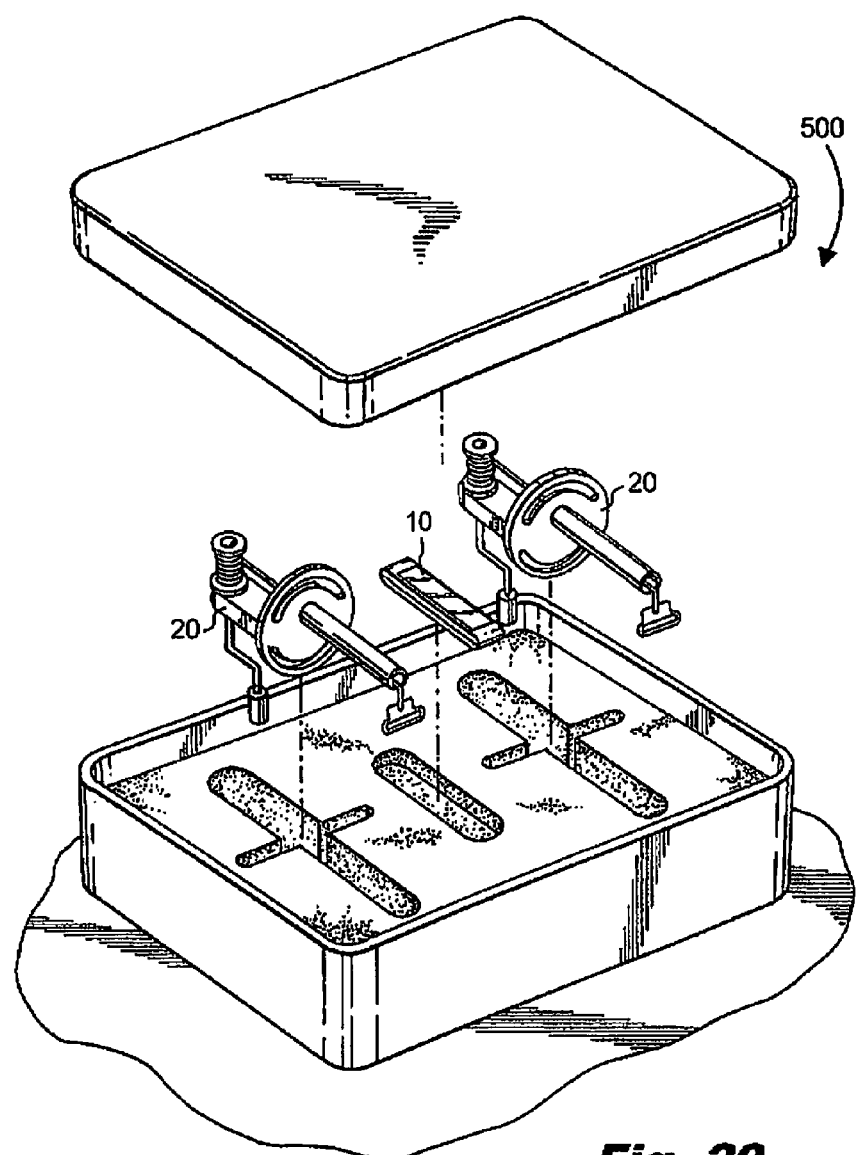
FIG. 20 is a perspective view of the laparoscopic scaffold assembly of FIG. 1 shown as a kit in accordance with the present disclosure.

Referring again to FIG. 1, each mover 20 includes a moving portion 30 and an anchor portion 40. The moving portion 30 includes a base 32, a crank 34, a spool 36 and a line 38 in the form of a suture. The crank 34 and spool 36 are rotatably mounted to the base 32. The line 38 is operably coupled to the spool 36 such that upon rotation of the crank 34, the line 38 extends and retracts with respect to the spool 36. The line 38 has an attachment feature 38a (e.g. a loop) disposed at the distal end thereof. The attachment feature can be any suitable shape such as an integrally formed ring "N" shown in FIG. 6 or an adjustable loop "AL" shown in FIG. 7. The anchor portion 40 includes a platform 42 for supporting the moving portion 30 and an insertion member in the form of a tubular member or cannula 44 extending therefrom for insertion within tissue through a tissue tract to access a body cavity "BC" (FIG. 3). The line 38 is adapted for movement through the cannula 44 upon the selective retraction and/or extension of the line 38 of each mover 20. The laparoscopic scaffold assembly may be assembled in the form of a kit 500 as illustrated in FIG. 20.

Figure 4:
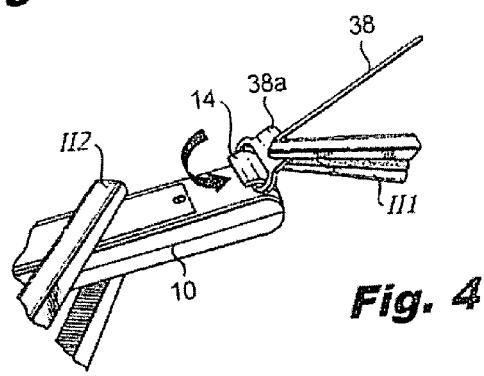
FIG. 4 is an enlarged perspective view illustrating the instrument pod of FIG. 2 being attached to a line extending from one of the movers.
Figure 5:
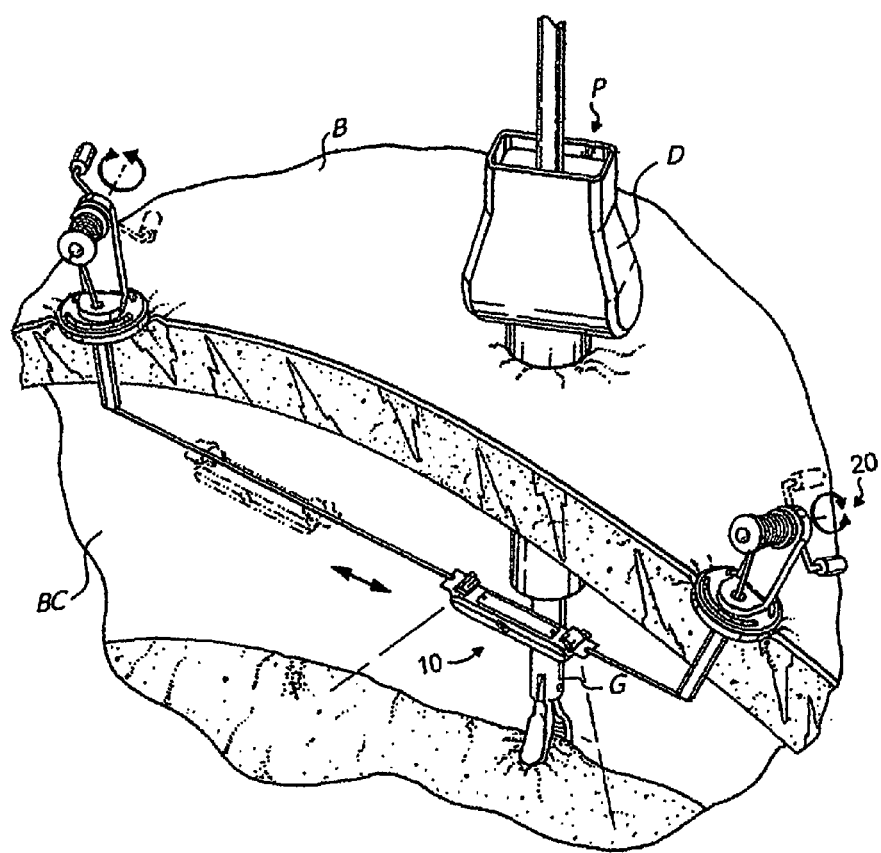
FIG. 5 is a perspective view of the laparoscopic scaffold assembly of FIG. 1 illustrating the instrument pod being movably suspended within the body cavity between each mover.
Figure 19:
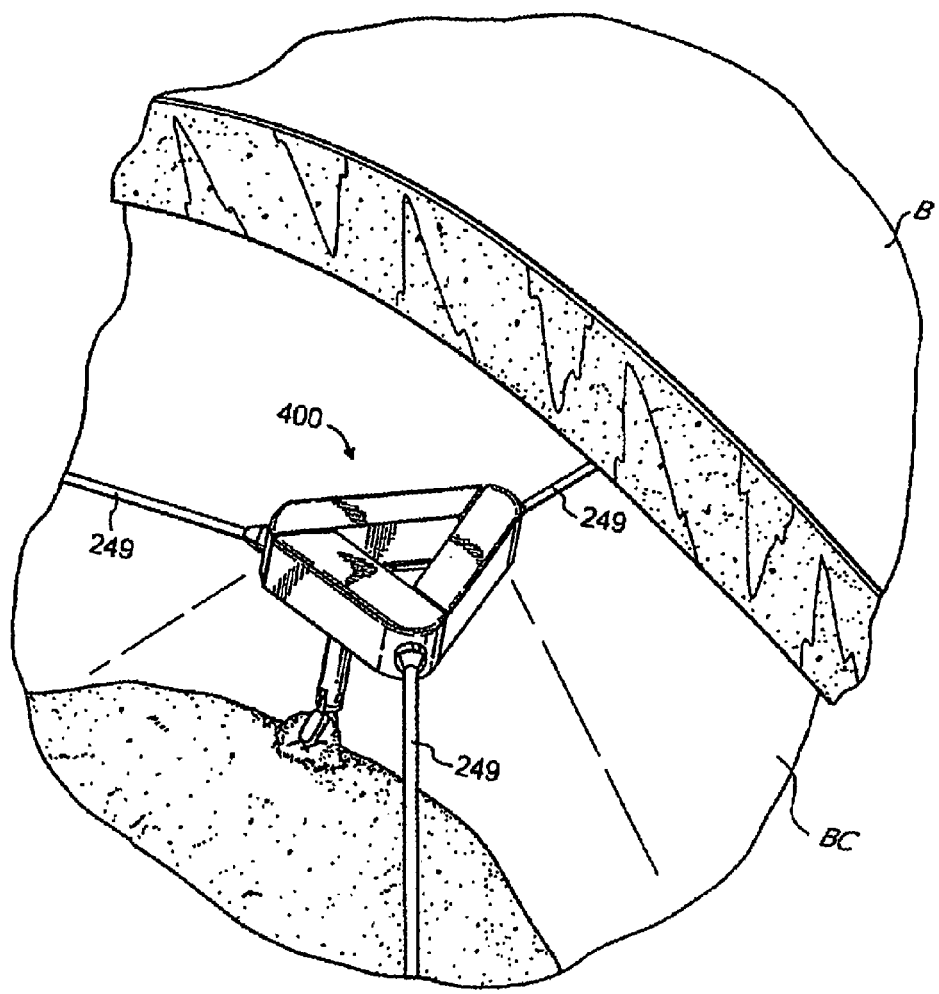
FIG. 19 is a perspective view of the instrument pod of FIGS. 16-18 shown positioned within a body cavity.

In use, shown best in FIGS. 3-5, each mover 20 is mounted to a patient's body "B" such that the cannula 44 extends into the body cavity "BC." The line 38 and attachment feature 38a of each mover 20 are adapted for movement through the cannula 44 upon rotation of the crank 34 and the extension and retraction of the line 38. An access device "D" is then mounted within the body cavity "BC." With reference to FIG. 3, the instrument pod 10 is then positioned in a vertically elongate condition so that it may be inserted through a longitudinal passage "P" of an access device "D" via a grasper "G" or other appropriate surgical instrumentation such as first instrument "I11" or second instrument "I12."

Once the instrument pod 10 is inserted through the longitudinal passage "P" and into the body cavity "BC", the attachment feature 38a of each mover 20 is then removably attached to the catches 12, 14 of the instrument pod 10 for movably suspending the instrument pod 10 in a substantially horizontally elongate condition within the body cavity "BC." As shown in FIG. 5, the instrument pod 10 can then be selectively movable between different positions (i.e. closer or further from one of the movers) relative to the movers 20 in response to the rotation the crank 34 of each mover 20 and the extension and retraction of each line 38. In this manner, the one or more suspended instruments "I" can be used in combination with the grasper "G" or other surgical instrumentation within the body cavity "BC." In addition, an accessory light or laparoscope "L" or other surgical instrumentation inserted into the body cavity "BC" may be mounted on or placed on the line 38 within the body cavity "BC" for providing additional or enhanced surgical benefits, as illustrated in FIG. 8. The illumination or instrumentation attached to instrument pod 10 can be moved along the line 38 to horizontally adjust their position by movement of the instrument pod 110 by the respective crank 34.

With reference to FIGS. 9 and 10, an alternate embodiment of a laparoscopic scaffold assembly 200 is illustrated. The assembly 200 includes an instrument pod 210 and a plurality of movers 220 such as movers 220a, 220b, 220c. The instrument pod 210 includes a plurality of ports 212 (FIG. 9)

disposed thereabout, e.g. at each of the vertices, for operably coupling to one or more lines 249 of the plurality of movers 220. The instrument pod 210 also includes one or more receptacles "R" on a lower surface (facing into the body cavity) adapted for receiving one or more instruments "I" (e.g., an illumination source, camera, etc, such as received by instrument pod 400 of FIG. 16) therein. As shown in FIG. 9, the one or more receptacles "R" each has an instrument "I" such as illumination source (e.g. light bulb) mounted therein. However, other instruments "I" may be mounted therein such as those discussed above and shown in FIG. 16 discussed below. In some embodiments, one or more of the plurality of ports 212 may be configured to send or receive wired signals through fiber optic wires or electrical wires operably associated with the one or more lines 249 of the movers 220. The fiber optic wires/cables or electrical wires/cables may be operably connected to the one or more ports 212 via a communication port such as a universal serial bus (USB), serial ports, parallel ports, or other suitable electrical connections operably coupled thereto. In some embodiments, these signals may be manually or automatically controlled by a central processing unit. In some embodiments, the instrument pod 210 may by configured for wireless communication with a power source and/or a controller such as a CPU or processor. The laparoscopic scaffold assembly 200 can include wireless technology for transmitting a signal. Thus, the movers 220 can be moved manually or powered remotely.

As illustrated in FIG. 9, the instrument pod 210 may be substantially triangularly shaped. In this manner, the instrument pod 210 may be coupled to three movers via lines extending therefrom which enables greater mobility thereof. This permits movement along the x-axis and the y-axis (see FIG. 10). That is, the pod 210 can be moved along the axis of the lines somewhat horizontal to the body cavity. The provision of three lines increases the stability of the platform. In some embodiments, the instrument pod may be formed of any suitable circular or noncircular shape (e.g. polygonal such as square, pentagonal, etc.), each of which may be operably connectable to any number of movers associated therewith to provide enhanced mobility.

Referring now to FIGS. 10-12, the plurality of movers 220 each include an anchoring portion 230 and a moving portion 240 that may be manually operable or electrically operable or fluid powered. As best shown in FIGS. 11-12, the anchoring portion 230 includes a body portion 232 having a T-shaped slot 232a, a clamp 234, and a fastener 236 so that the anchoring portion 230 may be affixed to a separate support "S" (e.g. a table or a ledge). The fastener 236, which operably couples the clamp 234 and the body portion 232, approximates and unapproximates the clamp 234 to the separate support "S" upon rotation of the fastener 236 so that the moving portion 240 and the anchoring portion 230 can be removably affixed to the separate support "S."

As shown in FIG. 11, the moving portion 240 includes an anchor 242 for engaging the slot 232a so that the moving portion 240 may be removably affixed to the anchoring portion 230 for interchanging or replacing moving portions 240 of movers 220a, 220b, 220c with respect to each anchoring portion 230. The moving portion 240 of each mover 220a, 220b, 220c includes a crank 244a, a spool 246, a base 248, and the one or more lines 249. The movers 220a, 220b, and 220c can be manually operable, electrically operable or both manually and electrically. They can also be fluid powered. By way of example, in the embodiment illustrated in FIG. 10, mover 220a has a crank 244a that is electrically operably, while mover 220b has a crank 244b that is electrically and manually operable, and mover 220c has a crank 244c that is only manually operable.

In some embodiments, electrically operable movers 220a, 220b may be operably coupled to a power source and a controller as illustrated in FIG. 10 or may be battery operated and actuable via one or more switches (not shown) to cause the spool 246 thereof to rotate, the one or more lines 249 to extend and retract, and the instrument pod 210 to move between the movers 220a, 220b, 220c. The manually operably movers 220b, 220c may include a knob 221 or a handle 223 for rotating the spool 246 thereof. Accordingly, each crank 244 and spool 246 is rotatably mounted to the base 248. The line 249 is operably coupled to the spool 246 such that upon rotation of the crank 244, the line 249 extends and retracts with respect to the spool 246. In some embodiments, the one or more lines 249 may include one or both of a fiber optic wire/cable or an electrical wire/cable, each of which may be housed within the one or more lines 249. In addition, the one or more lines 249 may be operably connected to a central processing unit "CPU" controller for selectively operating the laparoscopic scaffold assembly 200. Instead of a spool as described above, pinch rollers, timing belts, sprockets, and/or linear actuators such as air cylinders or solenoids, or other mechanisms, can be used to extend and retract the lines.

With reference to FIGS. 13-14, each line 249 may include an attachment feature such as the cylindrical shaped attachment feature 249a or the half cylindrical attachment feature 249b illustrated therein. Each attachment feature is configured to removably engage a port 212 (FIG. 9) in a side wall of pod 210 such as ports 212a, 212b of the instrument pod 210 such that the instrument pod 210 and each mover 220 are operably connected. As described above, ports 212a, 212b may include one or more universal serial buses (USB), serial ports, or parallel ports to send and receive signals to and from a power source and/or a controller.

Another embodiment of an instrument pod 310 is shown in FIG. 15. In this embodiment, the instrument pod 310 includes a body portion 310a having a pair of catches 312, 314 extending from the distal ends thereof and an instrument slot 316 configured to slidably receive a plurality of functional accessories. For example, instrument slot 316 may be configured to receive first accessory assembly 320 which includes a sensor 322. Similarly, instrument slot 316 may be configured to receive second accessory assembly 330 which includes a camera 332 and a surgical instrument engaging clip 334 for selectively affixing a plurality of surgical instruments thereto. However, any suitable instrument may be affixed thereto including an illumination source, a grasper, a retractor, a sensor, etc.

Referring now to FIGS. 16-19, an alternate embodiment of an instrument pod 400 includes a body portion 410 substantially triangular in configuration in the expanded condition. Body portion 410 has a plurality of sections 410a, 410b, 410c pivotably mounted thereto via a hinge 414 such that the instrument pod 400 is positionable between a collapsed condition (FIG. 18) for insertion through an access port or body opening into the body cavity and an expanded condition (FIG. 16). Each section 410a, 410b, 410c includes one or more ports 412 for operably coupling to one or more movers 220a, 220b, 220c in the mover similar to pod 210 discussed above. Each section 410a, 410b, 410c includes one or more instruments "I" (e.g., a camera, an illumination source, a grasper, a retractor, and a sensor) for performing a surgical procedure within a body cavity "BC."

It should be appreciated that a various number of moves can be utilized to provide the platform of the present disclosure. For example, instead of two movers, one mover and a spring can be provided. Additionally, instead of three movers, two movers and one or more springs could be provided. Also the pods can be of different shapes than shown.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of movably suspending an instrument pod within a body cavity, comprising:
    providing a scaffold assembly, comprising:
        at least one instrument operably associated with the instrument pod; and
        a plurality of movers, each mover including a tissue insertion member and at least one line extending therefrom, the at least one line being selectively extendable and retractable from each respective mover;
    inserting the instrument pod into the body cavity;
    attaching the at least one line of at least one of the movers to the instrument pod while the instrument pod and the at least one line are positioned within the body cavity; and
    selectively extending or retracting the at least one line such that the instrument pod moves within the body cavity.

2. The method of claim 1, further comprising selectively moving the instrument pod within the body cavity between two movers.

3. The method of claim 1, further comprising selectively moving the instrument pod within the body cavity between three movers.

4. The method of claim 1, further comprising selectively operating the at least one instrument within the body cavity wherein the at least one instrument includes at least one of a camera, an illumination source, a grasper, a retractor, and a sensor.

5. The method of claim 1, further comprising positioning the instrument pod between a first collapsed configuration and a second expanded configuration.

6. The method of claim 1, further comprising manually actuating at least one of the movers.

7. The method of claim 1, further comprising electrically actuating at least one of the movers.

8. The method of claim 1, wherein the instrument pod has an elongated configuration having first and second opposing end portions, the method further comprising:
    attaching a line of a first mover of the plurality of movers at the first end portion of the instrument pod; and
    attaching a line of a second mover of the plurality of movers at the second end portion of the instrument pod after insertion of the instrument pod into the body cavity.

9. The method of claim 1, attaching a line of a first mover of the plurality of movers to a first port of the instrument pod;
    attaching a line of a second mover of the plurality of movers to a second port of the instrument pod; and
    attaching a line of a third mover of the plurality of movers to a third port of the instrument pod.

10. The method of claim 1, further comprising attaching at least one of a camera, an illumination source, a grasper, a retractor, and a sensor to the instrument pod.

11. The method of claim 1, wherein attaching the at least one line includes attaching at least one of a fiber optic wire and an electrical wire to the instrument pod.

12. The method of claim 1, further comprising operatively coupling the at least one line to a CPU.

13. The method of claim 1, further comprising removing the at least one line from the instrument pod within the body cavity.

14. A method of movably suspending an instrument pod within a body cavity, comprising:
    inserting the instrument pod into the body cavity;
    attaching at least one line to the instrument pod while the instrument pod and the at least one line are positioned within the body cavity;
    operably associating the at least one line to a plurality of movers such that the at least one line is selectively extendable and retractable from each mover, the movers including a tissue insertion member; and
    selectively extending and retracting at least one line with at least one linear actuator operably associated with one or more of the plurality of movers to move the instrument pod within the body cavity.

15. The method of claim 14, further comprising positioning the instrument pod between a first collapsed configured and a second expanded configuration.

16. The method of claim 14, further comprising manually actuating at least one of the movers.

17. The method of claim 14, further comprising electrically actuating at least one of the movers.

18. The method of claim 14, further comprising attaching at least one of a camera, an illumination source, a grasper, a retractor, and a sensor to the instrument pod.

19. A method of manufacturing a scaffold assembly for minimally invasive surgery, comprising:
    configuring an instrument pod for insertion through a tissue tract into a body cavity;
    operably associating the instrument pod with a plurality of actuatable movers that are separate from the instrument pod and from one another;
    configuring a portion of each mover for insertion within tissue; and
    configuring at least one line of each mover for removable attachment to the instrument pod within the body cavity to enable each mover to move the instrument pod within the body cavity upon an actuation of at least one of the plurality of actuatable movers.

* * * * *